(12) United States Patent
Hubbard et al.

(10) Patent No.: US 6,514,617 B1
(45) Date of Patent: Feb. 4, 2003

(54) TAGGING MATERIALS FOR POLYMERS, METHODS, AND ARTICLES MADE THEREBY

(75) Inventors: Steven Frederick Hubbard, West Sand Lake, NY (US); Radislav Alexandrovich Potyrailo, Nishayuna, NY (US); Philippe Schottland, Evansville, IN (US); Verghese Thomas, Evansville, IN (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/901,966

(22) Filed: Jul. 11, 2001

(51) Int. Cl.$^7$ .......................... B32B 27/36; C08G 64/00
(52) U.S. Cl. ................. 428/412; 528/190; 528/193; 528/196; 528/271
(58) Field of Search ................ 528/176, 190, 528/193, 196, 271; 428/412

(56) References Cited

U.S. PATENT DOCUMENTS

| | | | |
|---|---|---|---|
| 4,238,524 A | 12/1980 | LaLiberte et al. | 427/7 |
| 5,005,873 A | 4/1991 | West | 283/92 |
| 5,201,921 A | 4/1993 | Luttermann et al. | 8/507 |
| 5,314,072 A | 5/1994 | Frankel et al. | 209/44.1 |
| 5,329,127 A | 7/1994 | Becker et al. | 250/459.1 |
| 5,510,619 A | 4/1996 | Zachmann et al. | 250/339.08 |
| 5,553,714 A | 9/1996 | Cushman et al. | 207/577 |
| 5,703,229 A | 12/1997 | Krutak et al. | 540/140 |
| 6,099,930 A | 8/2000 | Cyr et al. | 428/64.1 |
| 6,219,329 B1 | 4/2001 | Tanaka et al. | 369/275.1 |

FOREIGN PATENT DOCUMENTS

| | | |
|---|---|---|
| GB | 2264558 | 2/1993 |
| GB | 2330408 | 10/1997 |

*Primary Examiner*—Terressa M. Boykin
(74) *Attorney, Agent, or Firm*—Bernadette M. Bennett; Noreen C. Johnson

(57) ABSTRACT

A polymer comprising a tagging material is provided wherein the tagging material comprises at least one organic fluorophore dye, at least one inorganic fluorophore, at least one organometallic fluorophore, at least one semi-conducting luminescent nanoparticle, or combination thereof, wherein the tagging material has a temperature stability of at least about 350° C. and is present in a sufficient quantity such that the tagging material is detectible via a spectrofluorometer at an excitation wavelength in a range between about 100 nanometers and about 1100 nanometers. Further embodiments of the present invention include a method for identifying a polymer and an article comprising a polymer wherein the polymer contains the aforementioned tagging material.

69 Claims, 2 Drawing Sheets

TAGGING MATERIALS FOR POLYMERS, METHODS, AND ARTICLES MADE THEREBY

BACKGROUND OF THE INVENTION

The present invention is related to identification of polymer compositions. More particularly, the present invention is related to non-destructive identification of polymer compositions via spectroscopic tags.

Automated identification of plastic compositions is desirable for a variety of applications, such as recycling, tracking a manufacturing source, anti-piracy protection, and the like. Historically, X-rays and infrared spectroscopy have been used to identify plastic materials. Tagging materials such as ultraviolet and near-infrared fluorescent dyes have also been used for the identification of plastic compositions.

In Cyr et al., U.S. Pat. No. 6,099,930, tagging materials are placed in materials such as digital compact discs. A near-infrared fluorophore is incorporated into the compact disc via coating, admixing, blending, or copolymerization. Fluorescence is detectable when the fluorophore is exposed to electromagnetic radiation having a wavelength ranging from 670 nanometers to 1100 nanometers.

Unfortunately, the use of fluorophores may be problematic under certain conditions. For instance, if multiple fluorophores are used, there may be an inaccuracy in the signals that are produced if the dye ages or leaches under normal use conditions, which can include, for example, exposure to ultraviolet light and high ambient temperatures. Additionally, additives used in the polymer can alter the ratio of fluorescence intensities.

Due to the multitude of articles made by polymeric materials, there is a growing need to develop methods and tagging materials that a manufacturer can use to identify a product. Thus, methods and materials are constantly being sought which are effective, accurate, and easily detected.

BRIEF SUMMARY OF THE INVENTION

The present invention provides a method for identifying a polymer, comprising providing in the polymer at least one tagging material wherein the tagging material comprises at least one organic fluorophore dye, at least one inorganic fluorophore, at least one organometallic fluorophore, at least one semi-conducting luminescent nanoparticle, or combination thereof, wherein the tagging material has a temperature stability of at least 350° C. and is present in a sufficient quantity such that the tagging material is detectable via a spectrofluorometer at an excitation wavelength in a range between about 100 nanometers and about 1100 nanometers.

In a further embodiment of the present invention, a polymer is provided comprising a tagging material wherein the tagging material comprises at least one organic fluorophore dye, at least one inorganic fluorophore, at least one organometallic fluorophore, at least one semi-conducting luminescent nanoparticle, or combination thereof, wherein the tagging material has a temperature stability of at least 350° C. and is present in a sufficient quantity such that the tagging material is detectable via a spectrofluorometer at an excitation wavelength in a range between about 100 nanometers and about 1100 nanometers.

In yet a further embodiment of the present invention, an article is provided comprising a polymer wherein the polymer comprises at least one tagging material wherein the tagging material comprises at least one organic fluorophore dye, at least one inorganic fluorophore, at least one organometallic fluorophore, at least one semi-conducting luminescent nanoparticle, or combination thereof, wherein the tagging material has a temperature stability of at least 350° C. and is present in a sufficient quantity such that the tagging material is detectable via a spectrofluorometer at an excitation wavelength in a range between about 100 nanometers and about 1100 nanometers.

DETAILED DESCRIPTION OF THE INVENTION

Figure 1:
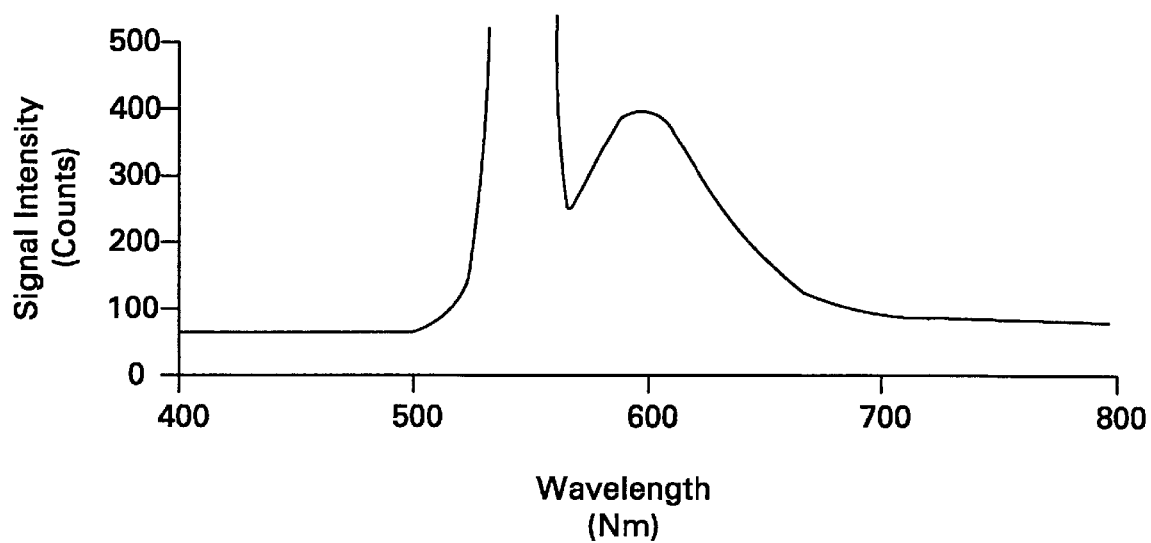
FIG. 1 depicts a fluorescence spectrum of a fluorescent tag incorporated into melt polycarbonate before a heat test as measured via a spectrofluorometer. Excitation wavelength, 546 nanometers.

The present invention relates to spectroscopic tags incorporated into polymers. Spectroscopic tags include at least one organic fluorophore, at least one inorganic fluorophore, at least one organometallic fluorophore, at least one semi-conducting luminescent nanoparticle, or combinations thereof. Spectroscopic tags make it possible to determine the thermal history and degradation of a polymer. In addition, the tagging materials used in the present invention are insensitive to polymer additives and to chemical and physical aging of the polymer.

These tagging materials are selected from classes of dyes that exhibit high robustness against ambient environmental conditions and temperature stability of at least about 350° C., preferably at least about 375° C., and more preferably at least about 400° C. Typically, the tagging materials have a temperature stability for a time period less than about 10 minutes and preferably, less than about 1 minute, and more preferably, less than 20 seconds.

The excitation range of these tagging materials is typically in a range between about 100 nanometers and about 1100 nanometers, and more typically in a range between about 200 nanometers and about 1000 nanometers, and most typically in a range between about 250 nanometers and about 950 nanometers. The emission range of these tagging materials is typically in a range between about 250 nanometers and about 2500 nanometers.

The tags of the present invention include organic, inorganic, or organometallic fluorophores. Exemplary fluorphores include, but are not limited to, known dyes such as polyazaindacenes or coumarins, including those set forth in U.S. Pat. No. 5,573,909. Other suitable families of dyes include lanthanide complexes, hydrocarbon and substituted hydrocarbon dyes; polycyclic aromatic hyrdocarbons; scintillation dyes (preferably oxazoles and oxadiazoles); aryl- and heteroaryl-substituted polyolefins ($C_2$–$C_8$ olefin portion); carbocyanine dyes; phthalocyanine dyes and pigments; oxazine dyes; carbostyryl dyes; porphyrin dyes; acridine dyes; anthraquinone dyes; arylmethane dyes; azo dyes; diazonium dyes; nitro dyes; quinone imine dyes; tetrazolium dyes; thiazole dyes; perylene dyes, perinone dyes, bis-benzoxazolylthiophene (BBOT), and xanthene dyes. Fluorophores of the present invention also include anti-stokes shift dyes which absorb in the near infrared wavelength and emit in the visible wavelength.

The following is a partial list of commercially available, suitable luminescent dyes.

5-Amino-9-diethyliminobenzo(a)phenoxazonium Perchlorate
7-Amino-4-methylcarbostyryl
7-Amino-4-methylcoumarin
7-Amino-4-trifluoromethylcoumarin
3-(2'-Benzimidazolyl)-7-N,N-diethylamninocoumarin
3-(2'-Benzothiazolyl)-7-diethylaminocoumarin
2-(4-Biphenylyl)-5-(4-t-butylphenyl)-1,3,4-oxadiazole
2-(4-Biphenylyl)-5-phenyl-1,3,4-oxadiazole
2-(4-Biphenyl)-6-phenylbenzoxazole-1,3
2,5-Bis-(4-biphenylyl)-1,3,4-oxadiazole
2,5-Bis-(4-biphenylyl)-oxazole
4,4'-Bis-(2-butyloctyloxy)-p-quaterphenyl
p-Bis(o-methylstyryl)-benzene
5,9-Diaminobenzo(a)phenoxazonium Perchlorate
4-Dicyanomethylene-2-methyl-6-(p-dimethylaminostyryl)-4H-pyran
1,1'-Diethyl-2,2'-carbocyanine Iodide
1,1'-Diethyl-4,4'-carbocyanine Iodide
3,3'-Diethyl-4,4',5,5'-dibenzothiatricarbocyanine Iodide
1,1'-Diethyl-4,4'-dicarbocyanine Iodide
1,1'-Diethyl-2,2'-dicarbocyanine Iodide
3,3'-Diethyl-9,11 -neopentylenethiatricarbocyanine Iodide
1,3'-Diethyl-4,2'-quinolyloxacarbocyanine Iodide
1,3'-Diethyl-4,2'-quinolylthiacarbocyanine Iodide
3-Diethylamino-7-diethyliminophenoxazonium Perchlorate
7-Diethylamino-4-methylcoumarin
7-Diethylamino-4-trifluoromethylcoumarin
7-Diethylaminocoumarin
3,3'-Diethyloxadicarbocyanine Iodide
3,3'-Diethylthiacarbocyanine Iodide
3,3'-Diethylthiadicarbocyanine Iodide
3,3'-Diethylthiatricarbocyanine Iodide
4,6-Dimethyl-7-ethylaminocoumarin
2,2'-Dimethyl-p-quaterphenyl
2,2-Dimethyl-p-terphenyl
7-Dimethylamino-1 -methyl-4-methoxy-8-azaquinolone-2
7-Dimethylamino-4-methylquinolone-2
7-Dimethylamino-4-trifluoromethylcoumarin
2-(4-(4-Dimethylaminophenyl)-1,3-butadienyl)-3-ethylbenzothiazolium Perchlorate
2-(6-(p-Dimethylaminophenyl)-2,4-neopentylene-1,3,5-hexatrienyl)-3-methylbenzothiazolium Perchlorate
2-(4-(p-Dimethylaminophenyl)-1,3-butadienyl)-1,3,3-trimethyl-3H-indolium Perchlorate
3,3'-Dimethyloxatricarbocyanine Iodide
2,5-Diphenylfuran
2,5-Diphenyloxazole
4,4'-Diphenylstilbene
1-Ethyl-4-(4-(p-Dimethylaminophenyl)-1,3-butadienyl)-pyridinium Perchlorate
1-Ethyl-2-(4-(p-Dimethylaminophenyl)-1,3-butadienyl)-pyridinium Perchlorate
1-Ethyl-4-(4-(p-Dimethylaminophenyl)-1,3-butadienyl)-quinolium Perchlorate
3-Ethylamino-7-ethylimino-2,8-dimethylphenoxazin-5-ium Perchlorate
9-Ethylamino-5-ethylamino-10-methyl-5H-benzo(a)phenoxazonium Perchlorate
7-Ethylamino-6-methyl-4-trifluoromethylcoumarin
7-Ethylamino-4-trifluoromethylcoumarin
1,1',3,3,3',3'-Hexamethyl-4,4',5,5'-dibenzo-2,2'-indotricarboccyanine Iodide
1,1',3,3,3',3'-Hexamethylindodicarbocyanine Iodide
1,1',3,3,3',3'-Hexamethylindotricarbocyanine Iodide
2-Methyl-5-t-butyl-p-quaterphenyl
N-Methyl-4-trifluoromethylpiperidino-<3,2-g>coumarin
3-(2'-N-Methylbenzimidazolyl)-7-N,N-diethylaminocoumarin
2-(1 -Naphthyl)-5-phenyloxazole
2,2'-p-Phenylen-bis(5-phenyloxazole)
3,5,3"",5""-Tetra-t-butyl-p-sexiphenyl
3,5,3"",5""-Tetra-t-butyl-p-quinquephenyl
2,3,5,6-1H,4H-Tetrahydro-9-acetylquinolizino-<9,9a,1-gh>coumarin
2,3,5,6-1H,4H-Tetrahydro-9-carboethoxyquinolizino-<9,9a,1-gh>coumarin
2,3,5,6-1H,4H-Tetrahydro-8-methylquinolizino-<9,9a,1-gh>coumarin
2,3,5,6-1H,4H-Tetrahydro-9-(3-pyridyl)-quinolizino-<9,9a,1-gh>coumarin
2,3,5,6-1H,4H-Tetrahydro-8-trifluoromethylquinolizino-<9,9a,1-gh>coumarin
2,3,5,6-1H,4H-Tetrahydroquinolizino-<9,9a,1-gh>coumarin
3,3',2",3'"-Tetramethyl-p-quaterphenyl
2,5,2"",5'"-Tetramethyl-p-quinquephenyl
P-terphenyl
P-quaterphenyl
Nile Red
Rhodamine 700
Oxazine 750
Rhodamine 800
IR 125
IR 144
IR 140
IR 132
IR 26
IR5
Diphenylhexatriene
Diphenylbutadiene
Tetraphenylbutadiene
Naphthalene
Anthracene
9,10-diphenylanthracene
Pyrene
Chrysene
Rubrene
Coronene
Phenanthrene.

The tags of the present invention may also include semi-conducting luminescent nanoparticles of sizes in a range between about 1 nanometer and about 50 nanometers. Exemplary semi-conducting luminescent nanoparticles include, but are not limited to, CdS, ZnS, $Cd_3P_2$, PbS, or combinations thereof. Semi-conducting luminescent nanoparticles also include rare earth aluminates including, but not limited to, strontium aluminates doped with Europium and Dysprosium.

In a preferred embodiment, tagging materials such as perylenes such as Anthra[2,1,9-def:6,5,10-d'e'f'] diisoquinoline-1,3,8,10(2H,9H)-tetrone, 2,9-bis[2,6-bis(1-methyethyl)phenyl]-5,6,12,13-tetraphenoxy are utilized.

Concentration of the tagging material depends on the quantum efficiency of the tagging material, excitation and emission wavelengths, and employed detection techniques, and can typically range from about $10^{-18}$ percent by weight and about 2 percent by weight of the total polymer, more typically range from about $10^{-15}$ percent by weight and about 0.5 percent by weight of the total polymer, and most typically range from about $10^{-12}$ percent by weight and about 0.05 percent by weight of the total polymer.

Some possible examples of polymers which can be utilized for the present invention include, but are not limited to, amorphous, crystalline and semi-crystalline thermoplastic materials: polyvinyl chloride, polyolefins (including, but not limited to, linear and cyclic polyolefins and including polyethylene, chlorinated polyethylene, polypropylene, and the like), polyesters (including, but not limited to, polyethylene terephthalate, polybutylene terephthalate, polycyclohexylmethylene terephthalate, and the like), polyamides, polysulfones (including, but not limited to, hydrogenated polysulfones, and the like), polyimides, polyether imides, polyether sulfones, polyphenylene sulfides, polyether ketones, polyether ether ketones, ABS resins, polystyrenes (including, but not limited to, hydrogenated polystyrenes, syndiotactic and atactic polystyrenes, polycyclohexyl ethylene, styrene-co-acrylonitrile, styrene-co-maleic anhydride, and the like), polybutadiene, polyacrylates (including, but not limited to, polymethylmethacrylate, methyl methacrylate-polyimide copolymers, and the like), polyacrylonitrile, polyacetals, polycarbonates, polyphenylene ethers (including, but not limited to, those derived from 2,6-dimethylphenol and copolymers with 2,3,6-trimethylphenol, and the like), ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, Teflons, as well as thermosetting resins such as epoxy, phenolic, alkyds, polyester, polyimide, polyurethane, mineral filled silicone, bis-maleimides, cyanate esters, vinyl, and benzocyclobutene resins, in addition to blends, copolymers, mixtures, reaction products and composites comprising at least one of the foregoing plastics.

As used herein, the terms "polycarbonate", "polycarbonate composition", and "composition comprising aromatic carbonate chain units" includes compositions having structural units of the formula (I):

(I)

in which at least about 60 percent of the total number of $R^1$ groups are aromatic organic radicals and the balance thereof are aliphatic, alicyclic, or aromatic radicals. Preferably, $R^1$ is an aromatic organic radical and, more preferably, a radical of the formula (II):

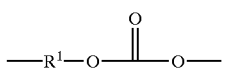

(II)

wherein each of $A^1$ and $A^2$ is a monocyclic divalent aryl radical and $Y^1$ is a bridging radical having one or two atoms which separate $A^1$ from $A^2$. In an exemplary embodiment, one atom separates $A^1$ from $A^2$. Illustrative, non-limiting examples of radicals of this type are —O—, —S—, —S(O)—, —S(O$_2$)—, —C(O)—, methylene, cyclohexylmethylene, 2-[2,2,1]-bicycloheptylidene, ethylidene, isopropylidene, neopentylidene, cyclohexylidene, cyclopentadecylidene, cyclododecylidene, and adamantylidene. The bridging radical $Y^1$ can be a hydrocarbon group or a saturated hydrocarbon group such as methylene, cyclohexylidene or isopropylidene.

Polycarbonates can be produced by the interfacial reaction of dihydroxy compounds in which only one atom separates $A^1$ and $A^2$. As used herein, the term "dihydroxy compound" includes, for example, bisphenol compounds having general formula (III) as follows:

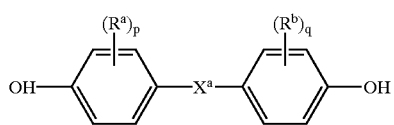

(III)

wherein $R^a$ and $R^b$ each represent a halogen atom or a monovalent hydrocarbon group and may be the same or different; p and q are each independently integers from 0 to 4; and $X^a$ represents one of the groups of formula (IV):

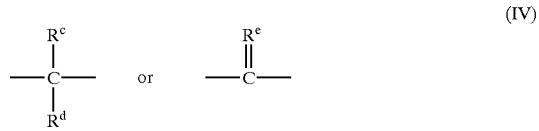

(IV)

wherein $R^c$ and $R^d$ each independently represent a hydrogen atom or a monovalent linear or cyclic hydrocarbon group and $R^e$ is a divalent hydrocarbon group.

Some illustrative, non-limiting examples of suitable dihydroxy compounds include dihydric phenols and the dihydroxy-substituted aromatic hydrocarbons disclosed by name or formula (generic or specific) in U.S. Pat. No. 4,217,438, which is incorporated herein by reference. A nonexclusive list of specific examples of the types of bisphenol compounds that may be represented by formula (III) includes the following: 1,1-bis(4-hydroxyphenyl)methane; 1,1-bis(4-hydroxyphenyl)ethane; 2,2-bis(4-hydroxyphenyl)propane (hereinafter "bisphenol A" or "BPA"); 2,2-bis(4-hydroxyphenyl)butane; 2,2-bis(4-hydroxyphenyl)octane; 1,1-bis(4-hydroxyphenyl)propane; 1,1-bis(4-hydroxyphenyl)n-butane; bis(4-hydroxyphenyl)phenylmethane; 2,2-bis(4-hydroxy-1-methylphenyl)propane; 1,1-bis(4-hydroxy-t-butylphenyl)propane; bis(hydroxyaryl)alkanes such as 2,2-bis(4-hydroxy-3-bromophenyl)propane; 1,1-bis(4-hydroxyphenyl)cyclopentane; and bis(hydroxyaryl)cycloalkanes such as 1,1-bis(4-hydroxyphenyl)cyclohexane; and the like as well as combinations comprising at least one of the foregoing.

It is also possible to employ polycarbonates resulting from the polymerization of two or more different dihydric phenols or a copolymer of a dihydric phenol with a glycol or with a hydroxy- or acid-terminated polyester or with a dibasic acid or with a hydroxy acid or with an aliphatic diacid in the event a carbonate copolymer rather than a homopolymer is desired for use. Generally, useful aliphatic diacids have from 2 to about 40 carbons. A preferred aliphatic diacid is dodecandioic acid. Polyarylates and polyester-carbonate resins or their blends can also be employed. Branched polycarbonates are also useful, as well as blends of linear polycarbonate and a branched polycarbonate. The branched polycarbonates may be prepared by adding a branching agent during polymerization.

These branching agents are well known and may comprise polyfunctional organic compounds containing at least three functional groups which may be hydroxyl, carboxyl, carboxylic anhydride, haloformyl and mixtures comprising at least one of the foregoing. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid and benzophenone tetracarboxylic acid, and the like. The branching agents may be added at a level of about 0.05 to about 2.0 weight percent. Branching agents and procedures for making branched polycarbonates are described in U.S. Pat. Nos. 3,635,895 and 4,001,184. All types of polycarbonate end groups are herein contemplated.

Preferred polycarbonates are based on bisphenol A, in which each of $A^1$ and $A^2$ is p-phenylene and $Y^1$ is isopropylidene. Preferably, the average molecular weight of the polycarbonate is about 5,000 to about 100,000, more preferably about 10,000 to about 65,000, and most preferably about 15,000 to about 35,000.

In monitoring and evaluating polycarbonate synthesis, it is of particular interest to determine the concentration of Fries product present in the polycarbonate. As noted, the generation of significant Fries product can lead to polymer branching, resulting in uncontrollable melt behavior. As used herein, the terms "Fries" and "Fries product" denote a repeating unit in polycarbonate having the formula (V):

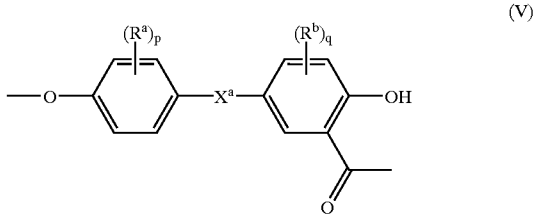

(V)

wherein $X^a$ is a bivalent radical as described in connection with Formula (III) described above.

The polycarbonate composition may also include various additives ordinarily incorporated in resin compositions of this type. Such additives are, for example, fillers or reinforcing agents; heat stabilizers; antioxidants; light stabilizers; plasticizers; antistatic agents; mold releasing agents; additional resins; blowing agents; and the like, as well as combinations comprising at least one of the foregoing additives. Examples of fillers or reinforcing agents include glass fibers, asbestos, carbon fibers, silica, talc and calcium carbonate. Examples of heat stabilizers include triphenyl phosphite, tris-(2,6-dimethylphenyl)phosphite, tris-(mixed mono- and di-nonylphenyl)phosphite, dimethylbenene phosphonate and trimethyl phosphate. Examples of antioxidants include octadecyl-3-(3,5-di-tert-butyl-4-hydroxyphenyl)propionate, and pentaerythrityl-tetrakis[3-(3,5-di-tert-butyl-4-hydroxyphenyl)propionate]. Examples of light stabilizers include 2-(2-hydroxy-5-methylphenyl) benzotriazole, 2-(2-hydroxy-5-tert-octylphenyl)-benzotriazole and 2-hydroxy-4-n-octoxy benzophenone. Examples of plasticizers include dioctyl-4,5-epoxy-hexahydrophthalate, tris-(octoxycarbonylethyl) isocyanurate, tristearin and epoxidized soybean oil. Examples of the antistatic agent include glycerol monostearate, sodium stearyl sulfonate, and sodium dodecylbenzenesulfonate. Examples of mold releasing agents include stearyl stearate, beeswax, montan wax and paraffin wax. Examples of other resins include but are not limited to polypropylene, polystyrene, polymethyl methacrylate, and polyphenylene oxide. Combinations of any of the foregoing additives may be used. Such additives may be mixed at a suitable time during the mixing of the components for forming the composition.

In addition to the polymer and tagging material, the composition may optionally include various additives ordinarily incorporated in resin compositions of this type. Such additives may include antioxidants, heat stabilizers, antistatic agents (tetra alkylammonium benzene sulfonate salts, tetra alkylphosphonium benzene sulfonate salts, and the like), mold releasing agents (pentaerythritol tetrastearate; glycerol monstearate, and the like), and the like, and combinations comprising at least one of the foregoing. For example, the substrate can comprise heat stabilizer in a range between about 0.01 weight percent and about 0.1 weight percent; an antistatic agent in a range between about 0.01 weight percent and about 0.2 weight percent; and a mold releasing agent in a range between about 0.1 weight percent and about 1 weight percent of a mold releasing agent; based upon the total weight of the polymer.

Some possible antioxidants include, for example, organophosphites, e.g., tris(nonyl-phenyl)phosphite, tris(2, 4-di-t-butylphenyl)phosphite, bis(2,4-di-t-butylphenyl) pentaerythritol diphosphite, distearyl pentaerythritol diphosphite and the like; alkylated monophenols, polyphenols and alkylated reaction products of polyphenols with dienes, such as, for example, tetrakis[methylene(3,5-di-tert-butyl-4-hydroxyhydrocinnamate)]methane, 3,5-di-tert-butyl-4-hydroxyhydrocinnamate octadecyl, 2,4-di-tert-butylphenyl phosphite, and the like; butylated reaction products of para-cresol and dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds, such as, for example, distearylthiopropionate, dilaurylthiopropionate, ditridecylthiodipropionate, and the like; amides of beta-(3,5-di-tert-butyl-4-hydroxyphenyl)-propionic acid; and the like, as well as combinations comprising at least one of the foregoing.

Other potential additives which may be employed comprise: UV absorbers; stabilizers such as light and thermal stabilizers (e.g., acidic phosphorous-based compounds); hindered phenols; zinc oxide, zinc sulfide particles, or combination thereof; lubricants (mineral oil, and the like), plasticizers, dyes used as a coloring material (quinines, azobenzenes, and the like); among others, as well as combinations comprising at least one of the foregoing additives.

In order to aid in the processing of the polymer, particularly polycarbonate, catalyst(s) may also be employed, namely in the extruder or other mixing device. The catalyst typically assists in controlling the viscosity of the resulting material. Possible catalysts include hydroxides, such as tetraalkylammonium hydroxide, tetraalkylphosphonium hydroxide, and the like, with diethyldimethylammonium hydroxide and tetrabutylphosphonium hydroxide preferred. The catalyst(s) can be employed alone or in combination with quenchers such as acids, such as phosphoric acid, and the like. Additionally, water may be injected into the polymer melt during compounding and removed as water vapor through a vent to remove residual volatile compounds.

The polymer is produced by using a conventional reaction vessel capable of adequately mixing various precursors, such as a single or twin screw extruder, kneader, blender, or the like. Spectroscopic tags can be incorporated into the polymer in the polymer manufacturing stage, during polymer processing into articles, or combinations thereof. The spectroscopic tag can be incorporated into the polymer such that it is uniformly dispersed throughout the polymer or such that it is dispersed on a portion of the polymer. The polymer precursors can be premixed with the spectroscopic tag (e.g., in a pellet, powder, and/or liquid form) and simultaneously fed through a hopper into the extruder, or the spectroscopic tag can be optionally added in the feed throat or through an alternate injection port of the injection molding machine or other molding. Optionally, the polymer can be produced and the spectroscopic tag can be dispersed on a portion of the polymer. Methods for incorporating the spectroscopic tag into the polymer include, for example, coating, admixing, blending, or copolymerization.

The extruder should be maintained at a sufficiently high temperature to melt the polymer precursors without causing decomposition thereof. For polycarbonate, for example, temperatures of about 220° C. to about 360° C. can be used, with about 260° C. to about 320° C. preferred. Similarly, the residence time in the extruder should be controlled to minimize decomposition. Residence times of up to about 2 minutes or more can be employed, with up to about 1.5 minutes preferred, and up to about 1 minute especially preferred. Prior to extrusion into the desired form (typically pellets, sheet, web, or the like, the mixture can optionally be filtered, such as by melt filtering and/or the use of a screen pack, or the like, to remove undesirable contaminants or decomposition products.

The polymers of the present invention may be used for any application in which the physical and chemical properties of the material are desired. Typically, the polymers are used for data storage media. After the polymer composition has been produced, it can be formed into a data storage media using various molding techniques, processing techniques, or combination thereof. Possible molding techniques include injection molding, film casting, extrusion, press molding, blow molding, stamping, and the like. One possible process comprises an injection molding-compression technique where a mold is filled with a molten polymer. The mold may contain a preform, inserts, fillers, etc. The polymer is cooled and, while still in an at least partially molten state, compressed to imprint the desired surface features (e.g., pits, grooves, edge features, smoothness, and the like), arranged in spiral concentric or other orientation, onto the desired portion(s) of the substrate, i.e. one or both sides in the desired areas. The substrate is then cooled to room temperature. Once the substrate has been produced, additional processing, such as electroplating, coating techniques (spin coating, spray coating, vapor deposition, screen printing, painting, dipping, and the like), lamination, sputtering, and combinations comprising at least one of the foregoing processing techniques, among others conventionally known in the art, may be employed to dispose desired layers on the substrate.

An example of a polycarbonate data storage media comprises an injection molded polycarbonate substrate which may optionally comprise a hollow (bubbles, cavity, and the like) or filled (metal, plastics, glass, ceramic, and the like, in various forms such as fibers, spheres, particles, and the like) core. Disposed on the substrate are various layers including: a data layer, dielectric layer(s), a reflective layer(s), and/or a protective layer, as well as combinations comprising at least one of the foregoing layers. These layers comprise conventional materials and are disposed in accordance with the type of media produced. For example, for a first surface media, the layers may be protective layer, dielectric layer, data storage layer, dielectric layer, and then the reflective layer disposed in contact with the substrate, with an optional decorative layer disposed on the opposite side of the substrate. Meanwhile, for an optical media, the layers may be optional decorative layer, protective layer, reflective layer, dielectric layer, and data storage layer, with a subsequent dielectric layer in contact with the substrate. Optical media may include, but is not limited to, any conventional pre-recorded, re-writable, or recordable formats such as: CD, CD-R, CD-RW, DVD, DVD-R, DVD-RW, DVD+RW, DVD-RAM, high-density DVD, magneto-optical, and others. It is understood that the form of the media is not limited to disk-shape, but may be any shape which can be accommodated in a readout device.

The data storage layer(s) may comprise any material capable of storing retrievable data, such as an optical layer, magnetic layer, or a magneto-optic layer. Typically the data layer has a thickness of up to about 600 Angstroms (Å) or so, with a thickness up to about 300 Å preferred. Possible data storage layers include, but are not limited to, oxides (such as silicone oxide), rare earth elements—transition metal alloys, nickel, cobalt, chromium, tantalum, platinum, terbium, gadolinium, iron, boron, others, and alloys and combinations comprising at least one of the foregoing, organic dye (e.g., cyanine or phthalocyanine type dyes), and inorganic phase change compounds (e.g., TeSeSn, InAgSb, and the like).

The protective layer(s), which protect against dust, oils, and other contaminants, can have a thickness of greater than about 100 microns ($\mu$) to less than about 10 Å, with a thickness of about 300 Å or less preferred in some embodiments, and a thickness of about 100 Å or less especially preferred. The thickness of the protective layer(s) is usually determined, at least in part, by the type of read/write mechanism employed, e.g., magnetic, optic, or magneto-optic. Possible protective layers include anti-corrosive materials such as gold, silver, nitrides (e.g., silicon nitrides and aluminum nitrides, among others), carbides (e.g., silicon carbide and others), oxides (e.g., silicon dioxide and others), polymeric materials (e.g., polyacrylates or polycarbonates), carbon film (diamond, diamond-like carbon, and the like), among others, and combinations comprising at least one of the foregoing.

The dielectric layer(s), which are disposed on one or both sides of the data storage layer and are often employed as heat controllers, can typically have a thickness of up to or exceeding about 1,000 Å and as low as about 200 Å or less. Possible dielectric layers include nitrides (e.g., silicon nitride, aluminum nitride, and others); oxides (e.g., aluminum oxide); carbides (e.g., silicon carbide); and combinations comprising at least one of the foregoing materials, among other materials compatible within the environment and preferably not reactive with the surrounding layers.

The reflective layer(s) should have a sufficient thickness to reflect a sufficient amount of energy (e.g., light) to enable data retrieval. Typically the reflective layer(s) can have a thickness of up to about 700 Å or so, with a thickness of about 300 Å to about 600 Å generally preferred. Possible reflective layers include any material capable of reflecting the particular energy field, including metals (e.g., aluminum, silver, gold, titanium, and alloys and mixtures comprising at least one of the foregoing metals, and others).

In addition to the data storage layer(s), dielectric layer(s), protective layer(s) and reflective layer(s), other layers can be employed such as lubrication layer and others. Useful lubricants include fluoro compounds, especially fluoro oils and greases, and the like.

The tagging materials of the present invention allows for a non-destructive means for the tracking of materials, determination of processing conditions such as the temperature at which an article was manufactured in addition to the thermal history and degradation.

In order that those skilled in the art will be better able to practice the invention, the following example is given by way of illustration and not by way of limitation.

EXAMPLE

An organic fluorophore (Lumogen Red 300 obtained from BASF) was used as a spectroscopic tag. It has a high melting point (300° C.) and high temperature stability. The tag was incorporated into the melt polycarbonate material during the melt polymerization reaction. The melt polymerization was performed in a lab reactor. For heat stability tests, small amounts of polymer (about 0.5 grams) were put into an oven at 400° C. for three minutes. Heating of the samples was done in air.

Fluorescence emission spectra of the tag before and after the heating test were performed to assess the temperature stability of the tag. Determinations were performed on a setup which included a white light source (450 Watt Xenon arc lamp, SLM Instruments, Inc., Urbana, Ill., Model FP-024), a monochromator for selection of the excitation wavelengths (SLM Instruments, Inc., Model FP-092) and a portable spectrofluorometer (Ocean Optics, Inc., Dunedin, Fla., Model ST2000). The spectrofluorometer was equipped with a 200 micron slit, 600 groves per millimeter grating blazed at 400 nanometers and covering the spectral range from 250 to 800 nanometers with efficiency greater than 30% and a linear charge coupled device (CCD) array detector. Light from the monochromator was focused into one of the arms of a "six-around-one" bifurcated fiber-optic reflection probe (Ocean Optics, Inc., Model R400-7-UV/VIS). Light from the samples was collected when the common end of the fiber-optic probe was position near the samples at a certain angle to minimize the amount of light directly reflected from the sample back into the probe. The second arm of the probe was coupled to the spectrofluorometer.

Figure 2:
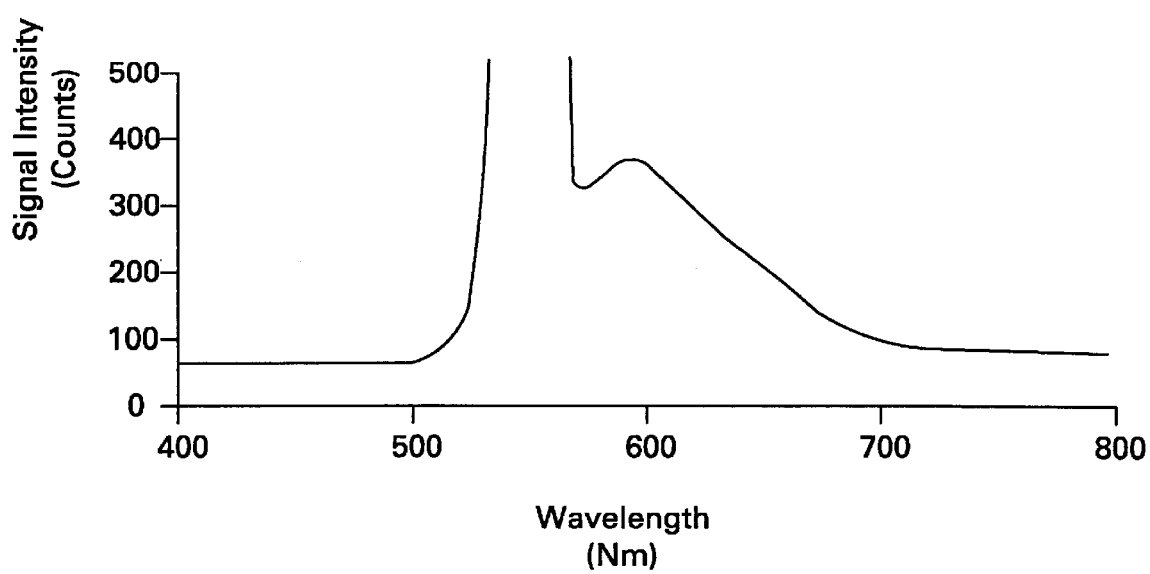
FIG. 2 depicts a fluorescence spectrum of a fluorescent tag incorporated into melt polycarbonate after a heat test as measured via a spectrofluorometer. Excitation wavelength, 546 nanometers.

FIG. 1 depicts the fluorescence spectrum of the fluorescent tag incorporated into melt polycarbonate before the heat test. Excitation wavelength was 546 nanometers. FIG. 2 depicts the fluorescence spectrum of the fluorescent tag incorporation into melt polycarbonate after the heat test. Excitation wavelength was 546 nanometers. This data clearly illustrates that the optical media made of polycarbonate and tagged with the disclosed fluorescent tagging dye can be processed above 350° C. Such temperature is comparable with the temperature of DVD production.

While embodiments have been shown and described, various modifications and substitutions may be made thereto without departing from the spirit and the scope of the invention. Accordingly, it is to be understood that the present invention has been described by way of illustration and not limitation.

What is claimed is:

1. A method for identifying a polymer, comprising providing in the polymer at least one tagging material wherein the tagging material comprises at least one organic fluorophore dye, at least one inorganic fluorophore, at least one organometallic fluorophore, at least one semi-conducting luminescent nanoparticle, or combination thereof, wherein the tagging material has a temperature stability of at least about 350° C. and is present in a sufficient quantity such that the tagging material is detectable via a spectrofluorometer at an excitation wavelength in a range between about 100 nanometers and about 1100 nanometers.

2. The method in accordance with claim 1, wherein the tagging material has a temperature stability of at least about 375° C.

3. The method in accordance with claim 1, wherein the tagging material has a temperature stability of at least about 400° C.

4. The method in accordance with claim 1, wherein the tagging material has an excitation wavelength in a range between about 200 nanometers and about 1000 nanometers.

5. The method in accordance with claim 4, wherein the tagging material has an excitation wavelength in a range between about 250 nanometers and about 950 nanometers.

6. The method in accordance with claim 1, wherein the at least one fluorophore dye comprises perylenes.

7. The method in accordance with claim 6, wherein the at least one fluorophore dye comprises anthra[2,1,9-def:6,5,10-d'e'f']diisoquinoline-1,3,8,10(2H,9H)-tetrone, 2,9-bis[2,6-bis(1-methyethyl)phenyl]-5,6,12,13-tetraphenoxy, or combinations thereof.

8. The method in accordance with claim 1, wherein at least one fluorophore dye comprises a lanthanide complex.

9. The method in accordance with claim 1, wherein the fluorophore is an anti-stokes shift dye.

10. The method in accordance with claim 1, wherein at least one semi-conducting luminescent nanoparticle comprises CdS, ZnS, $Cd_3P_2$, PbS, or combinations thereof.

11. The method in accordance with claim 1, wherein at least one semi-conducting luminesent nanoparticle comprises rare earth aluminates comprising strontium aluminates doped with Europium and Dysprosium.

12. The method in accordance with claim 1, wherein the tagging material is present in a range between about $10^{-18}$ and about 2 percent by weight of the total polymer.

13. The method in accordance with claim 12, wherein the tagging material is present in a range between about $10^{-15}$ and about 0.5 percent by weight of the total polymer.

14. The method in accordance with claim 13, wherein the tagging material is present in a range between about $10^{-12}$ and about 0.05 percent by weight of the total polymer.

15. The method of claim 1, wherein the polymer comprises a thermoplastic polymer material.

16. The method of claim 15, wherein the thermoplastic polymer material comprises polycarbonate.

17. The method of claim 1, wherein the tagging material is incorporated into the polymer by coating, admixing, blending, or copolymerization.

18. The method of claim 1, wherein the polymer is used in a storage media for data.

19. The method of claim 1, wherein the polymer contains a coloring material.

20. The method in accordance with claim 1, wherein the tagging material has a temperature stability for a time period of less than about 10 minutes.

21. The method in accordance with claim 1, wherein the tagging material has a temperature stability for a time period of less than about 1 minute.

22. The method in accordance with claim 1, wherein the tagging material has a temperature stability for a time period of less than about 20 seconds.

23. A method for identifying a polycarbonate, comprising providing in the polycarbonate at least one tagging material wherein the tagging material comprises a perylene, wherein the perylene has a temperature stability of at least about 350° C., is present in a range between about $10^{-18}$ percent by weight and about 2 percent by weight of the total polycarbonate and is detectable via a spectrofluorometer at an excitation wavelength in a range between about 100 nanometers and about 1100 nanometers.

24. A polymer comprising a tagging material wherein the tagging material comprises at least one organic fluorophore dye, at least one inorganic or organometallic fluorophore, at least one semi-conducting luminescent nanoparticle, or combination thereof, wherein the tagging material has a temperature stability of at least about 350° C. and is present in a sufficient quantity such that the tagging material is detectable via a spectrofluorometer at an excitation wavelength in a range between about 100 nanometers and about 1100 nanometers.

25. The polymer in accordance with claim 24, wherein the tagging material has a temperature stability of at least about 375° C.

26. The polymer in accordance with claim 24, wherein the tagging material has a temperature stability of at least about 400° C.

27. The polymer in accordance with claim 24, wherein the at least one fluorophore dye has an excitation wavelength in a range between about 200 nanometers and about 1000 nanometers.

28. The polymer in accordance with claim 27, wherein the at least one fluorophore dye has an excitation wavelength in a range between about 250 nanometers and about 950 nanometers.

29. The polymer in accordance with claim 24, wherein the at least one fluorophore dye comprises perylenes.

30. The polymer in accordance with claim 29, wherein the at least one fluorophore dye comprises anthra[2,1,9-def:6,5,10-d'e'f']diisoquinoline-1,3,8,10(2H,9H)-tetrone, 2,9-bis[2,6-bis(1-methyethyl)phenyl]-5,6,12,13-tetraphenoxy, or combinations thereof.

31. The polymer in accordance with claim 24, wherein the at least one fluorophore dye comprises a lanthanide complex.

32. The polymer in accordance with claim 24, wherein the fluorphore comprises an anti-stokes shift dye.

33. The polymer in accordance with claim 24, wherein the at least one semi-conducting luminescent nanoparticle comprises CdS, ZnS, $Cd_3P_2$, PbS, or combinations thereof.

34. The polymer in accordance with claim 24, wherein the at least one semi-conducting luminescent nanoparticles comprises rare earth aluminates comprising strontium aluminates doped with Europium and Dysprosium.

35. The polymer in accordance with claim 24, wherein the tagging material is present in a range between about $10^{-18}$ percent by weight and 2 percent by weight of the total polymer.

36. The polymer in accordance with claim 35, wherein the tagging material is present in a range between about $10^{-15}$ percent by weight and about 0.5 percent by weight of total polymer.

37. The polymer in accordance with claim 36, wherein the tagging material is present in a range between about $10^{-12}$ percent by weight and about 0.05 percent by weight of total polymer.

38. The polymer in accordance with claim 24, wherein the polymer comprises a thermoplastic polymer material.

39. The polymer in accordance with claim 38, wherein the thermoplastic polymer material comprises polycarbonate.

40. The polymer in accordance with claim 24, wherein the tagging material is incorporated into the polymer by coating, admixing, blending, or copolymerization.

41. The polymer in accordance with claim 24, wherein the polymer is used in a storage media for data.

42. The polymer in accordance with claim 24 comprising a coloring material.

43. The polymer in accordance with claim 24, wherein the tagging material has a temperature stability for a time period of less than about 10 minutes.

44. The polymer in accordance with claim 24, wherein the tagging material has a temperature stability for a time period of less than about 1 minute.

45. The polymer in accordance with claim 24, wherein the tagging material has a temperature stability for a time period of less than about 20 seconds.

46. A polycarbonate comprising a perylene, wherein the perylene has a temperature stability of at least about 350° C. and is present in a range between about $10^{-18}$ percent by weight and about 2 percent by weight of the total polycarbonate and is detectible via a spectrofluorometer at an excitation wavelength in a range between about 100 nanometers and about 1100 nanometers.

47. An article comprising a polymer wherein the polymer comprises at least one tagging material wherein the tagging material comprises at least one organic fluorophore dye, at least one semi-conducting luminescent nanoparticle, or combination thereof, wherein the tagging material has a temperature stability of at least about 350° C. and is present in a sufficient quantity such that the tagging material is detectible via a spectrofluorometer at an excitation wavelength in a range between about 100 nanometers and about 1100 nanometers.

48. The article in accordance with claim 47, wherein the tagging material has a temperature stability of at least about 375° C.

49. The article in accordance with claim 47, wherein the tagging material has a temperature stability of at least about 400° C.

50. The article in accordance with claim 47, wherein the at least one fluorophore dye has an excitation wavelength in a range between about 200 nanometers and about 1000 nanometers.

51. The article in accordance with claim 50, wherein the at least one fluorophore dye has an excitation wavelength in a range between about 250 nanometers and about 950 nanometers.

52. The article in accordance with claim 47, wherein the at least one fluorophore dye comprises perylenes.

53. The article in accordance with claim 52, wherein the at least one fluorophore dye comprises anthra[2,1,9-def:6,5,10-d'e'f']diisoquinoline-1,3,8,10(2H,9H)-tetrone, 2,9-bis[2,6-bis(1-methyethyl)phenyl]-5,6,12,13-tetraphenoxy, or combinations thereof.

54. The article in accordance with claim 47, wherein at least one fluorophore dye comprises a lanthanide complex.

55. The article in accordance with claim 47, wherein the fluorophore is an anti-stokes shift dye.

56. The article in accordance with claim 47, wherein at least one semi-conducting luminescent nanoparticle comprises CdS, ZnS, $Cd_3P_2$, PbS, or combinations thereof.

57. The article in accordance with claim 47, wherein at least one semi-conducting luminescent nanoparticle comprises rare earth aluminates comprising strontium aluminates doped with Europium and Dysprosium.

58. The article in accordance with claim 47, wherein the tagging material is present in a range between about $10^{-18}$ to about 2 percent by weight of the total polymer.

59. The article in accordance with claim 58, wherein the tagging material is present in a range between about $10^{-15}$ to about 0.5 percent by weight of the total polymer.

60. The article in accordance with claim 59, wherein the tagging material is present in a range between about $10^{-12}$ to about 0.05 percent by weight of the total polymer.

61. The article in accordance with claim 47, wherein the polymer comprises a thermoplastic polymer material.

62. The article in accordance with claim 61, wherein the thermoplastic polymer material comprises polycarbonate.

63. The article in accordance with claim 47, where in the tagging material is incorporated in to the polymer by coating, admixing, blending, or copolymerization.

64. The article in accordance with claim 47, wherein the polymer is used in a storage media for data.

65. The article in accordance with claim 47, wherein the polymer contains a coloring material.

66. The article in accordance with claim 47, wherein the tagging material has a temperature stability for a time period of less than about 10 minutes.

67. The article in accordance with claim 47, wherein the tagging material has a temperature stability for a time period of less than about 1 minute.

68. The article in accordance with claim 47, wherein the tagging material has a temperature stability for a time period of less than about 20 seconds.

69. A storage medium for data comprising a polycarbonate wherein the polycarbonate comprises a perylene wherein the perylene has a temperature stability of at least about 350° C., is present in a range between about $10^{-18}$ percent by weight and about 2 percent by weight of the total polycarbonate, and is detectabile via a spectrofluorometer at an excitation wavelength in a range between about 100 nanometers and about 1100 nanometers.

* * * * *